United States Patent [19]

Kurokawa et al.

[11] Patent Number: 5,993,847
[45] Date of Patent: Nov. 30, 1999

[54] METHOD FOR IMPROVING REPRODUCTION ACTIVITY OF BOARS BY USING FEED

[75] Inventors: Satoru Kurokawa; Kiyoshi Hashimoto; Yasushi Yoshimi; Hiroaki Matsumura; Takahisa Tokunaga, all of Tokyo; Toshiaki Kono; Akihiro Kodaira, both of Saitama, all of Japan

[73] Assignee: Meija Seika Kaisha, Ltd., Tokyo, Japan

[21] Appl. No.: 08/501,447

[22] Filed: Jul. 12, 1995

[30] Foreign Application Priority Data

Feb. 3, 1995 [JP] Japan ................................. 7-016601

[51] Int. Cl.⁶ ............................ A61K 9/14; A23K 1/00
[52] U.S. Cl. .............................. 424/442; 426/2; 426/658
[58] Field of Search ............................ 424/442; 426/2, 426/658

[56] References Cited

U.S. PATENT DOCUMENTS 4,788,065  11/1988  Nakamura et al. ................... 426/2

FOREIGN PATENT DOCUMENTS

| 133547 | 5/1985 | European Pat. Off. . |
| 171026 | 2/1986 | European Pat. Off. . |
| 549478 | 6/1993 | European Pat. Off. . |
| 83899 | 6/1970 | Germany . |
| 63-024858 | 2/1988 | Japan . |
| 05210897 | 8/1993 | Japan . |

OTHER PUBLICATIONS

E.T. Kornegay, et al, "Effectiveness and Safety of Fructo–o––Ligosaccharides for Pigs, "*Animal Science Research Report, Virginia Agricultural Experiment Station*, No. 10, pp. 19–20 (1992).

*Primary Examiner*—Thurman K. Page
*Assistant Examiner*—James M. Spear
*Attorney, Agent, or Firm*—Sughrue, Mion, Zinn, Macpeak & Seas, PLLC

[57] ABSTRACT

This invention aims at improving the breeding activity of boars, especially at preventing the reduction of fertilization capacity in the hot season. Particularly, this invention provides a method for improving the breeding activity of boars with the use of a feed for breeding boars which contains saccharides mainly composed of oligosaccharides.

6 Claims, No Drawings

METHOD FOR IMPROVING REPRODUCTION ACTIVITY OF BOARS BY USING FEED

FIELD OF THE INVENTION

This invention relates to a method for improving the breeding activity of boars by feeding the breeding boars with a feed which contains saccharides mainly composed of oligosaccharides. The invention aims at rendering possible the stable conception and the provision of spermatozoa throughout the year, particularly by preventing a reduction in fertilization capacity in the hot season.

BACKGROUND OF THE INVENTION

With the recent tendency of Japanese eating habits toward the Western style, the demand for meat has been increasing. Therefore, meat manufactures need to develop an effective feeding method. On the other hand, the Japanese livestock industry should further improve productivity to compete on the world market.

Examples of methods for improving productivity in the pig industry include enlargement of the litter size, elevation of the rate of raising infants, and increment of the farrowing frequency. Although the litter size and the rate of raising newborns have improved by progress in livestock breeding and by improvements of feeding management facility and environmental sanitation, these effects are still insufficient.

On the other hand, improvement of the conception rate or prevention of breeding maladies is another important subject for the improvement of productivity. In order to breed pigs, it is necessary to repeat the cycle of estrus, mating, conception and farrowing efficiently. However, the generation of breeding maladies has been increasing in recent years because, for example, of the difficulty in closely observing each pig for feeding management due to the expanding management scale of pig farms, thus causing significant managerial loss.

In the case of pigs, a decrease in their breeding activities in the hot season is a problem which should be resolved. Its boar-side causes include the onset of diseases such as orchitis and the like, a lack and decrease in copulative passion, the deterioration of semen conditions and the like in the hot season. Especially, it is substantially difficult to check the deterioration of semen conditions in the case of natural mating, for example, so that it is mostly past hope when a breeding malady in boars is found. In addition, since semen conditions in the hot season are unstable, preservable days of semen are also reduced by half, hence posing another problem from the viewpoint of artificial fertilization.

In consequence, in order to effect an improvement of the breeding activity or the prevention of breeding maladies, various means have been attempted such as the administration of antibiotics and hormones. However, such means are not always sufficient enough because of additional problems in terms of side effects or safety of the feed. Because of this, great concern has been directed toward the development of a means by which breeding activity can be improved efficiently with less labor and cost, particularly a means which renders possible stable conception and provision of spermatozoa throughout the year by preventing a decrease in the fertilization capacity of boars in the hot season.

SUMMARY OF THE INVENTION

The present inventors have conducted extensive studies in order to overcome the aforementioned problems. As a result, they have successfully discovered for the first time that a feed which contains saccharides mainly composed of oligosaccharides has excellent effects. The present invention has been accomplished on the basis of this finding.

Accordingly, the present invention relates to a method for improving the fertilization capacity of spermatozoa with the use of a feed for breeding boars which contains saccharides mainly composed of oligosaccharides. Especially, this invention aims at rendering possible the stable conception and the provision of spermatozoa throughout the year by preventing the reduction of fertilization capacity in boars during the hot season.

Other objects and advantages of the present invention will be made apparent as the description progresses.

DETAILED DESCRIPTION OF THE INVENTION

Examples of the oligosaccharide to be used in the present invention include fructooligosaccharides, galactooligosaccharides, inulooligosaccharides, soybean oligosaccharides, lactulose, isomaltooligosaccharides, lactosucrose, xylooligosaccharides and the like. In particular, oligosaccharides in which a plurality of fructose molecules are linked as a constituent, such as fructooligosaccharides or inulooligosaccharides, is particularly preferred.

The saccharides containing fructooligosaccharides as the main component, to be used in the present invention, are for example a saccharide composition obtained by treating sucrose with a fructose transferase (see JP-A-56-154967; the term "JP-A" as used herein means an "unexamined published Japanese patent application"), which is a mixture of fructooligosaccharides in which 1 to 4 fructose molecules are linked to sucrose with sucrose, glucose, fructose and the like. This saccharide composition may be manufactured, for example, by the following method.

BS medium containing 5.0% sucrose, 1.0% peptone, 0.7% boullion and 0.3% sodium chloride was placed in two test tubes (10 ml each) and sterilized at 120° C. for 30 minutes. One A"zeful sample of *Aspergillus niger* (The genus Aspergillus, Williams & Wilkins Corporation, 1965, Item 293) was inoculated to each test tube and incubated at 28° C. for 24 hours. The culture thus obtained was then inoculated to two conical flasks each containing 200 ml of BS medium previously sterilized at 120° C. for 30 minutes (10 ml of culture to each), and subjected to shake culture at 28° C. for 24 hours, giving a master culture.

Twenty liters of BS medium was charged in a 30-liter jar fermentor, sterilized at 120° C. for 30 minutes and, cooled. The master culture prepared above (a total of 400 ml) was inoculated to this medium, and cultivated at 28° C. for 72 hours with aeration and agitation (300 rpm). At the end of cultivation, microbial cells were filtered off, and 20 liters of the filtrate was concentrated and purified by ultra-filtration, giving 2 liters of an enzyme solution (enzyme activity: 240 unit/ml).

Separately, 10 kg of sucrose was dissolved in 6.7 liters of water, and the pH of the resulting solution was adjusted to 5.0. To this solution was added the enzyme solution prepared above in an amount of 48 units per gram of sucrose and the mixture was held at 50° C. for 48 hours to complete transformation. At the end of reaction, the mixture was heated at 100° C. for 15 minutes to deactivate the enzyme, and decolorized by addition of activated charcoal (0.5% on solid base). After removal of the charcoal, the filtrate was treated with ion-exchange resins (Amberlite IR120B and Amberlite IRA411) and then concentrated, affording 12 kg of a sugar composition consisting of 33% glucose (G), 2% fructose (F), 10% sucrose (GF), 25% 1-kestose (GF2), 25% nistose (GF3) and 5% fructosylnistose (GF4).

According to the present invention, a feed for breeding boars which contains saccharides containing fructooligosaccharides as the main component (hereinafter, sometime referred to simply as "FO") is obtained by adding the afore-mentioned FO to an ordinary feed for breeding boars. The amount of FO to be added is not particularly limited, but, when effect, profitability and the like are taken into consideration, the objectives of the present invention may be fully obtained by adding the FO in an amount of 0.1 to 2 parts by weight, preferably 0.1 to 0.6 parts by weight, per 100 parts by weight of the feed. As occasion demands, other nutrition supplementing materials such as vitamins, oils and fats and the like may further be added.

In the practice of the method of the present invention, it is desirable to feed boars with the inventive feed continuously throughout the year, with an approximate feeding amount as FO per animal of generally from 2.7 to 54 g/day, preferably from 2.7 to 16.2 g/day. As a matter of course, the amount may be optionally changed depending on the physical conditions of the boars, the seasons and the like. Especially, in order to prevent the reduction of the fertilization capacity of the boars in the hot season, it is necessary to carry out continuous feeding at least over a period of from March to August.

As shown in the following inventive examples, the inventive method was able to improve the in vitro fertilization ratio, the normality and concentration of spermatozoa in the FO feeding group and, especially, to prevent the reduction of fertilization capacity in boars in the hot season. These results show that a stable fertilization capacity can be expected in artificial fertilization throughout the year.

Since collected semen is used in artificial fertilization after diluting it 30 to 40 times, the dilution ratio exerts great influence upon the conception ratio in many cases and therefore is restricted by seasons and spermatozoa conditions. However, the stable and high fertilization capacity of spermatozoa effected by the inventive method renders possible a higher dilution of semen and therefore its provision to larger numbers of sows by one semen collection.

Examples of the present invention are given below by way of illustration and not by way of limitation.

INVENTIVE EXAMPLE 1

Boars were continuously fed with an FO-containing feed to examine its effect on semen.
(1) Outline of the Test:
A total of 6 boars were divided into a control group and a test group, each group containing 3 animals. A commercially available feed for breeding boars was used in both groups in an equal amount. In the test group, the commercial feed was mixed with Meiji Feed Oligo SI (manufactured by Meiji Seika Kaisha, Ltd.; FO content, about 27%) in an amount of 10 g/day/head and used as the feed of the present invention. Taking effects of feeding on the fertilization capacity in the hot season into consideration, the test was carried out over a period of from March to December.
(2) Items Tested:
In vitro fertilization ratio, normality and concentration of spermatozoa were measured in the ordinary method described, in Yoshida M. et al., "Confocal and fluorescence microscopic study using lectins of the distribution of cortical granules during maturation and fertilization of pig oocytes", *Mol. Reprod. Dev.*, vol. 36, pp. 462–468 (1993) and Yoshida M. et al., "Birth of piglets derived from in vitro fertilization of pig oocytes matured in vitro", *Theriogenology*, vol. 39, pp. 1303–1311 (1993). These measurements were carried out in July, August, September and October when effects of the hot season were likely to occur.
(3) Results:
The results are shown in Table 1. As is evident from the table, in comparison with the control group, continuous feeding of the feed of the present invention in the test group is effective in improving the in vitro fertilization ratio, the normality and concentration of spermatozoa and in preventing the reduction of fertilization capacity in boars in the hot season.

TABLE 1

| Items | Groups | July | August | September | October |
| --- | --- | --- | --- | --- | --- |
| In vitro fertilization | control | 59.3 ± 28.0 | 76.7 ± 14.5 | 47.3 ± 6.4 | 26.7 ± 12.6 |
| ratio (%) | test | 75.8 ± 6.9 | 68.6 ± 20.9 | 61.6 ± 18.1 | 65.2 ± 21.8 |
| Spermatozoa normality | control | 83.8 ± 2.7 | 87.5 ± 0.9 | 82.2 ± 6.6 | 81.6 ± 4.9 |
| ratio (%) | test | 85.1 ± 4.3 | 81.8 ± 2.8 | 87.3 ± 3.7 | 87.1 ± 4.2 |
| Spermatozoa concentration | control | 4.2 ± 1.8 | 4.5 ± 0.8 | 6.8 ± 2.8 | 4.2 ± 0.9 |
| (×100 million/ml) | test | 5.3 ± 0.2 | 5.2 ± 1.0 | 5.6 ± 1.1 | 6.2 ± 1.9 |

Note
data, average ± SEM

Thus, according to the present invention, the breeding activity of boars can be improved and the reduction of fertilization capacity can be prevented, especially in the hot season, by the use of feed for breeding boars which contains saccharides mainly composed of oligosaccharides. Because of this, a method which renders the possible stable conception and the provision of spermatozoa throughout the year can be provided easily with low cost. This invention greatly contributes to the stable breeding activity of pigs throughout the year, especially for improving the conception frequency.

While the invention has been described in detail and with reference to specific examples thereof, it will be apparent to one skilled in the art that various changes and modifications can be made therein without departing from the spirit and scope thereof.

What is claimed is:

1. A method for improving reproduction activity of boars which comprises feeding breeding boars a feed that contains saccharides mainly composed of oligosaccharides continuously throughout the year, in an approximate feeding amount per animal of 2.7 to 54 g/day.

2. The method as set forth in claim 1, wherein said oligosaccharides are fructooligosaccharides.

3. A method for improving reproduction activity of boars which comprises feeding breeding boars a feed that contains saccharides mainly composed of oligosaccharides, wherein said boars are fed the feed continuously from March through August, in an approximate feeding amount per animal of 2.7 to 54 g/day.

4. A boar reproduction method which comprises:
(a) feeding breeding boars a feed that contains saccharides mainly composed of oligosaccharides, wherein said boars are fed the feed continuously from March through August, in an approximate feeding amount per animal of 2.7 to 54 g/day;
(b) mating the breeding boars fed according to step (a).

5. A boar reproduction method as set forth in claim 4 wherein the oligosaccharides are fructooligosaccharides.

6. A boar reproduction method as set forth in claim 4 wherein the step (b) is an artificial fertilization or a collection of semen.

* * * * *